(12) United States Patent
Je et al.

(10) Patent No.: US 7,903,785 B2
(45) Date of Patent: Mar. 8, 2011

(54) METHOD OF BRIGHT-FIELD IMAGING USING X-RAYS

(75) Inventors: Jung Ho Je, Gyeongsangbuk-do (KR); Jae Mok Yi, Gyeongsangbuk-do (KR)

(73) Assignees: Postech Foundation (KR); Postech Academy-Industry Foundation (KR)

( * ) Notice: Subject to any disclaimer, the term of this patent is extended or adjusted under 35 U.S.C. 154(b) by 244 days.

(21) Appl. No.: 12/373,278

(22) PCT Filed: Jul. 12, 2006

(86) PCT No.: PCT/KR2006/002735
§ 371 (c)(1),
(2), (4) Date: Jan. 9, 2009

(87) PCT Pub. No.: WO2008/007817
PCT Pub. Date: Jan. 17, 2008

(65) Prior Publication Data
US 2009/0290681 A1 Nov. 26, 2009

(51) Int. Cl.
*G01N 23/201* (2006.01)

(52) U.S. Cl. .............................. 378/87; 378/84
(58) Field of Classification Search .................. 378/70, 378/71, 73, 76, 84, 86–90
See application file for complete search history.

(56) References Cited

U.S. PATENT DOCUMENTS

| | | | |
|---|---|---|---|
| 5,016,267 A | 5/1991 | Wilkins | |
| 5,148,457 A | 9/1992 | Kubota et al. | |
| 5,802,137 A | 9/1998 | Wilkins | |
| 5,850,425 A | 12/1998 | Wilkins | |

*Primary Examiner* — Jurie Yun
(74) *Attorney, Agent, or Firm* — Harness, Dickey & Pierce, P.L.C.

(57) ABSTRACT

Provided is a method of bright-field imaging using x-rays in a sample to reveal lattice defects as well as structural inhomogeneities, the method comprising: (a) disposing a sample on a holder in the Laue transmission geometry and setting the sample to a single reflection in the Bragg diffraction; (b) projecting a beam of monochromatic x-rays on the sample; and (c) obtaining transmitted radiographic images and reversed diffracted images of the projected beam of monochromatic x-rays by the sample, respectively.

14 Claims, 4 Drawing Sheets

[Figure 1]
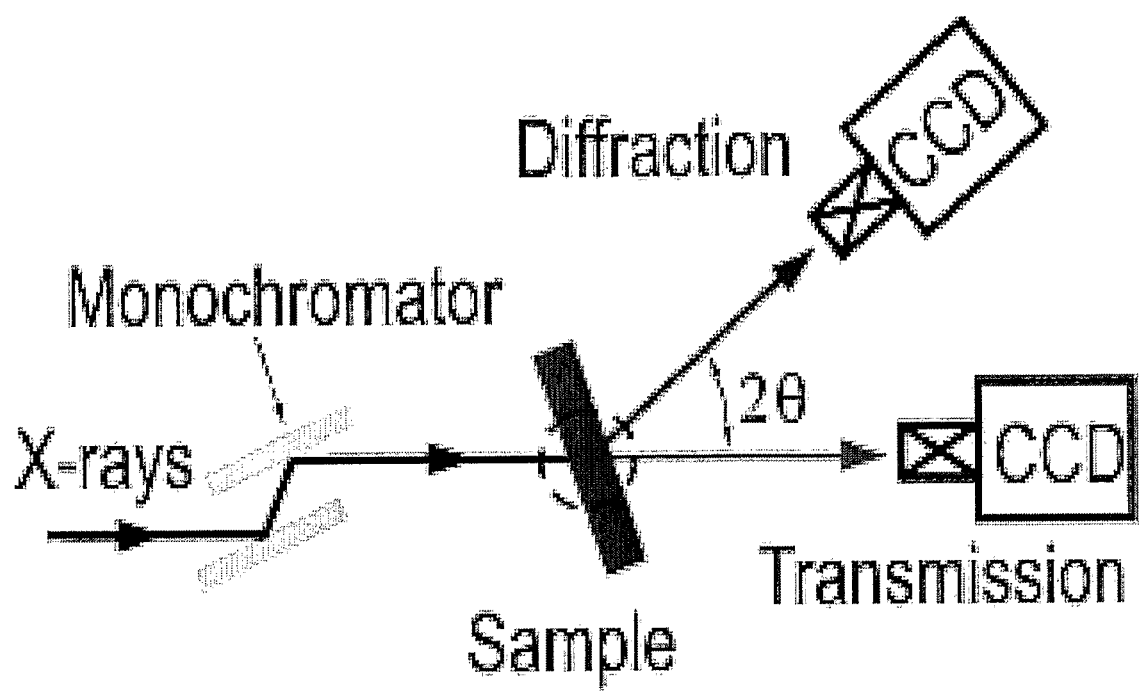

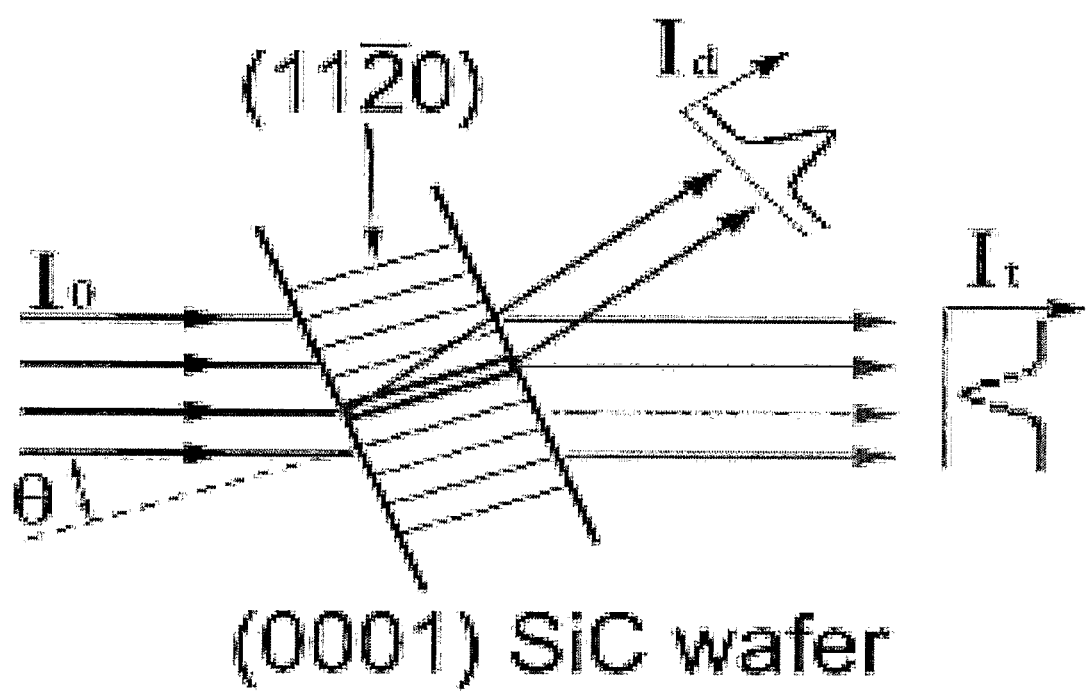
[Figure 2]

[Figure 3]
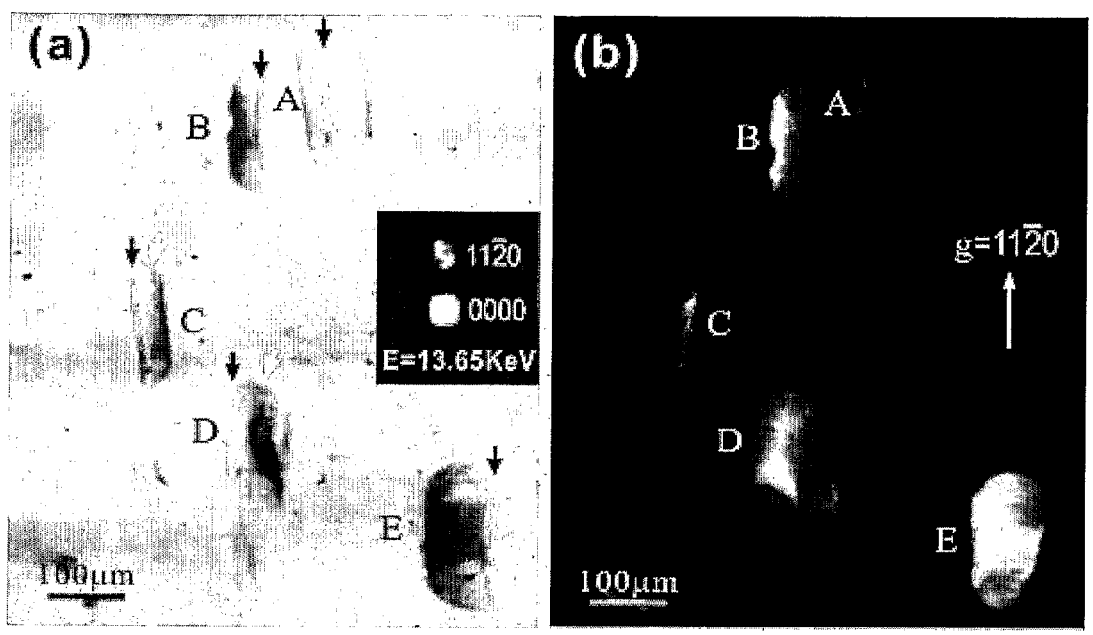

[Figure 4]
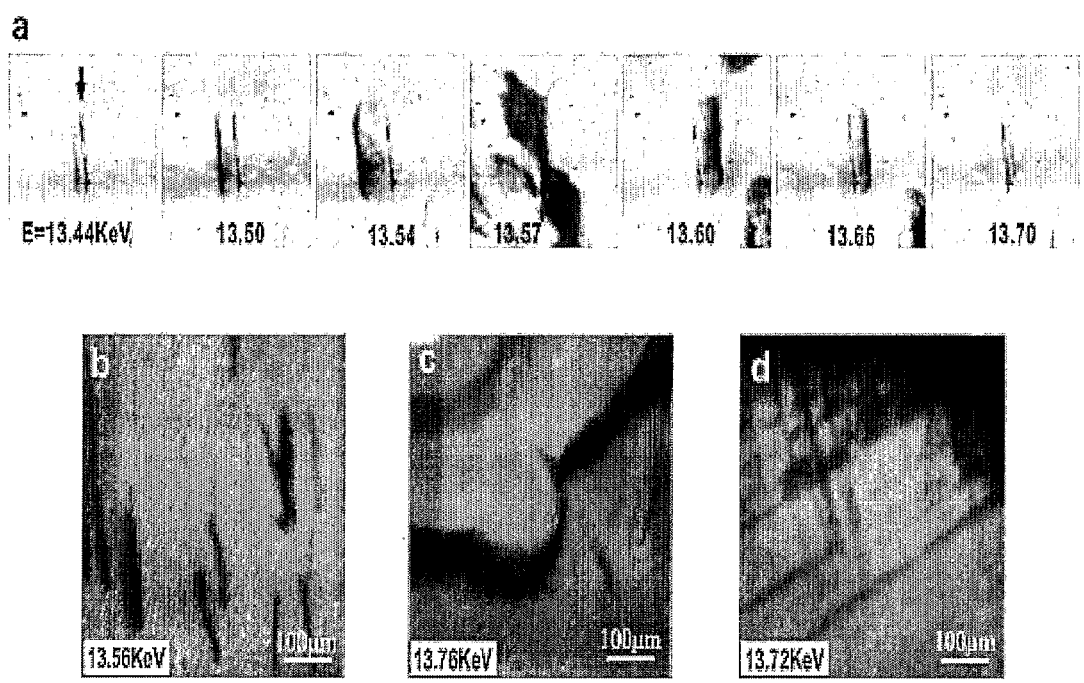

METHOD OF BRIGHT-FIELD IMAGING USING X-RAYS

CROSS-REFERENCE TO RELATED APPLICATIONS

This application is a U.S. 371 National Stage Application of International Application No. PCT/KR2006/002735, filed on Jul. 12, 2006 and published in English as WO 2008/007817 on Jan. 17, 2008. The disclosure of the above applications is incorporated herein by reference.

TECHNICAL FIELD

The present invention relates to a method of bright-field imaging of crystalline materials using x-rays.

BACKGROUND ART

Bright-field (BF) images are well known in transmission electron microscopy (TEM): images created by unscattered electrons are entirely due to mass-thickness variations in amorphous sample but may include diffraction contrast in crystalline samples. On the contrary, no x-ray images were so far obtained that carry diffraction-created information and standard radiographic information.

In conventional X-ray imaging of crystalline materials, the image contrast is basically due to either strain effect or phase gradient. Strain contrast, generally measurable in diffracted beam by X-ray topography, reveals local lattice displacements. Phase gradient, arising across transmitted beam due to phase object (Cloetens, 1996), allows measuring structural inhomogeneities by phase-contrast radiology (Wilkins, 1996; Hwu, 1999).

DISCLOSURE OF INVENTION

Technical Problem

Up to now, however, X-ray imaging, in contrast with electron, has not been successful for simultaneously acquiring strain contrast and phase gradient from one image.

Technical Solution

It is therefore a primary object of the invention to provide a novel technique that allows simultaneous investigation of lattice defects and structural inhomogeneities in crystalline materials at high precision in a short time.

To achieve this object, the present invention provides a method of bright-field imaging using x-rays in a sample to reveal lattice defects as well as structural inhomogeneities, the method comprising the steps of: (a) disposing a sample on a holder in the Laue transmission geometry and setting the sample to a single reflection in the Bragg diffraction; (b) projecting a beam of monochromatic x-rays on the sample; and (c) obtaining transmitted radiographic images and reversed diffracted images of the projected beam of monochromatic x-rays by the sample, respectively.

Preferably, the single reflection of the sample satifies two conditions given by:
a strong intensity reflection; and a perfect in-plane reflection.

Preferably, the perfect in-plane reflection is for plane (11$\bar{2}$0).

Preferably, the sample comprises a single crystal material.
Preferably, the single crystal material is SiC wafer.

Preferably, the projecting of the beam of monochromatic x-rays on the sample is performed either with changing energy of the beam of monochromatic x-rays either or with rocking the sample.

Preferably, the changing of the energy of the beam of monochromatic x-rays is in the range from −0.2 kev to 0.2 keV.

Preferably, the beam of monochoromatic x-rays is prepared by a Si (111) double-bounce monochromator.

Preferably, wherein the beam of monochromatic x-rays is collimated.

Preferably, the images are obtained from converting the transmitted beam of monochromatic x-rays into visible lights through a scintillation crystal.

Preferably, the scintillation crystal is $CdWO_4$.

Preferably, the lattice defects include dislocations, mosaicity, grainboundaries, an lattice plane bending in the sample.

Preferably, the structural inhomogeneities include grains, edges, voids, hollow tube, and ribbon type of defects in the sample.

Preferably, the beam of monochromatic x-rays has the energy of 13.65 keV, and the angle of 17° with a normal of the sample surface.

ADVANTAGEOUS EFFECTS

The present invention is based on using collimated monochromatic x-rays to obtain radiographs similar to bright-field TEM images with both kinds of information, specifically revealing lattice defects as well as structural inhomogeneities. According to the invention, a novel technique that allows simultaneous investigation of lattice defects and structural inhomogeneities in crystalline materials at high precision in a short time is provided.

BRIEF DESCRIPTION OF THE DRAWINGS

The above aspects and features of the present invention will be more apparent by describing embodiments of the present invention with reference to the accompanying figures, in which:

FIG. 1 is a schematic representation of an apparatus of BF x-ray imaging according to one preferred embodiment of this invention, wherein the x-ray beam is incident from the left and is monochromatized by the Si(1,1,1) crystal. This beam is incident on the sample in the Laue transmission geometry. This beam is transmitted and also diffracted through the sample. The transmitted beam is detected as an image on a lens-coupled high-resolution CCD camera system.

FIG. 2 is Schematic illustration of contrast inversion between transmitted (BF) and diffracted (DF) beams due to Bragg diffraction.

FIG. 3(a) shows an example of BF imaging under the above optimal conditions (E=13.65 KeV, θ=17 degree); the Laue pattern in the inset demonstrates the strong reflection.

FIG. 3(b) is an complementary DF image of the same reflection.

FIG. 4(a) is BF images for different photon energies E showing displacements of the 1120 lattice plane around a micropipe (the black arrow). FIGS. 4(b)-4(d) BF images showing lattice distortions associated with micropipes with full-core, lattice planebending and grain boundaries. Best Mode for Carrying Out the Invention

BEST MODE FOR CARRYING OUT THE INVENTION

The experiments were performed at the XOR 2-BM beamline of the Advanced Photon Source, USA. The experimental setup is shown in FIGS. 1 and 2.

An energy tunable monochromatic x-ray beam is provided by a Si(111) double-bounce monochromator.

A lens-coupled high-resolution CCD camera system was used for imaging the beam intensity. High-resolution transmission images (Koch, 1998) were obtained by converting x-rays into visible light with $CdWO_4$ scintillation crystal and then focusing the light into the 1 k×1 k CCD chip through a 20× objective lens—reaching a 0.65 μm effective pixel resolution.

Samples of (0001) 4H—SiC wafers (0.3-0.45 mm thickness, 30 mm diameter) were prepared from different crystals grown by the sublimation method.

The CCD detection system was placed 200 mm away from the sample to obtain radiographic phase-contrast in transmission images.

By detecting the diffracted beam, we also obtained the equivalent of dark-field (DF) TEM images; in this case, the CCD system was placed 5 mm from the sample to enhance the spatial resolution.

In principle, any sample position angle and x-ray photon energy E could produce diffraction effects in the transmission (BF) images. In practice, we could only detect them after adopting two conditions: (1) a single reflection with strong intensity, and (2) perfect in-plane (vertical to the wafer surface) reflections. Theoretical simulation and empirical tests led us to select the 11$\bar{2}$0 plane as the optimal reflection for BF imaging in SiC.

The black arrows in FIG. 3(a) identify micropipes (hollow tube superdislocations) penetrating through the wafer thickness. Border enhancement by phase contrast makes these very small (0.1~1 μm in diameter) features clearly visible.

Additional features marked by the white arrows are explained instead by diffraction since they are dark (diffraction-caused loss of intensity) and drastically change with E. This interpretation is validated by the DF image of the same reflection in FIG. 3(b). It is clearly seen correspondence and complementary contrast of the BF diffraction features and the DF features. Thus, even without DF imaging, BF radiographs can be used to study lattice distortions. This approach allows a one-to-one correlation between sample and image, in contrast with diffraction (DF) imaging where the correlations can be disturbed by overlap and/or separation of diffracted X-rays with different directions.

Preliminary tests of our BF imaging were performed to identify different types of lattice defects. FIG. 4(a) shows the E-dependence of the dark features revealing the spatial distribution of 11$\bar{2}$0 lattice planes around a micropipe. This approach could quantitatively study aspects of the local dislocations during micropipe formation such as strain field magnitudes, the Burgers vector sign, the hollow-core size, etc. FIG. 4(b) shows dark-contrast features with no radiographic contrast, therefore due to fill-core micropipes. The long dark contrast feature (bend contour) in FIG. 4(c) reveals the existence of lattice plane bending and its E-dependence can be used to estimate the type and direction of the bent. The orthogonal network in FIG. 4(d) shows grain boundaries probably caused by large lattice plane bending during the crystal growth.

INDUSTRIAL APPLICABILITY

Following the successful results described here, this invention can be applied to a variety of crystalline systems to simultaneously study structural inhomogeneities such as micropipes or voids and local lattice distortions due to strain fields, mosaicity or grain boundaries.

The invention claimed is:

1. A method of bright-field imaging using x-rays in a sample to reveal lattice defects as well as structural inhomogeneities, the method comprising the steps of:
   (a) disposing a sample on a holder in the Laue transmission geometry and setting the sample to a single reflection in the Bragg diffraction;
   (b) projecting a beam of monochromatic x-rays on the sample; and
   (c) obtaining transmitted radiographic images and reversed diffracted images of the projected beam of monochromatic x-rays by the sample, respectively.

2. The method of claim 1, wherein, the single reflection of the sample satisfies two conditions given by:
   a strong intensity reflection; and a perfect in-plane reflection.

3. The method of claim 2, wherein the perfect in-plane reflection is for plane (1120).

4. The method of claim 1, wherein the sample comprises a single crystal material.

5. The method of claim 4, wherein the single crystal material is SiC wafer.

6. The method of claim 1, wherein the projecting of the beam of monochromatic x-rays on the sample is performed either with changing energy of the beam of monochromatic x-rays or with rocking the sample.

7. The method of claim 6, wherein the changing of the energy of the beam of monochromatic x-rays is in the range from −0.2 kev to 0.2 keV.

8. The method of claim 1, wherein the beam of monochromatic x-rays is prepared by a Si (111) double-bounce monochromator.

9. The method of claim 1, wherein the beam of monochromatic x-rays is collimated.

10. The method of claim 1, wherein the images are obtained from converting the transmitted beam of monochromatic x-rays into visible lights through a scintillation crystal.

11. The method of claim 10, wherein the scintillation crystal is $CdWO_4$.

12. The method of claim 1, wherein the lattice defects include dislocations, mosaicity, grainboundaries, an lattice plane bending in the sample.

13. The method of claim 1, wherein the structural inhomogeneities include grains, edges, voids, hollow tube, and ribbon type of defects in the sample.

14. The method of claim 1, wherein the beam of monochromatic x-rays has the energy of 13.65 keV, and the angle of 17° with a normal of the sample surface.

* * * * *